(12) United States Patent
Gustavsson (10) Patent No.: US 8,808,275 B2
(45) Date of Patent: Aug. 19, 2014

(54) CATHETER ASSEMBLY COMPRISING A RECEPTACLE ACCOMMODATING A CATHETER AND A WETTING FLUID POUCH

(75) Inventor: Evelina Gustavsson, Öjersjö (SE)

(73) Assignee: Astra Tech Ab, Molndal (SE)

( * ) Notice: Subject to any disclaimer, the term of this patent is extended or adjusted under 35 U.S.C. 154(b) by 0 days.

(21) Appl. No.: 13/114,225

(22) Filed: May 24, 2011

(65) Prior Publication Data

US 2011/0295239 A1     Dec. 1, 2011

Related U.S. Application Data

(60) Provisional application No. 61/348,104, filed on May 25, 2010.

(30) Foreign Application Priority Data

May 25, 2010   (EP) ..................................... 10163767

(51) Int. Cl.
*A61M 5/00*     (2006.01)
(52) U.S. Cl.
USPC ........... 604/544; 604/171; 604/172; 604/265; 604/328
(58) Field of Classification Search
None
See application file for complete search history.

(56) References Cited

U.S. PATENT DOCUMENTS 4,057,047 A      11/1977  Gossett
2009/0200186 A1*  8/2009  Nestenborg et al. .......... 206/364

FOREIGN PATENT DOCUMENTS

| WO | WO 01/43807 A1 | 6/2001 | |
| WO | 01/52763 | * 7/2001 | ............. A61B 19/02 |
| WO | WO 01/52763 A1 | 7/2001 | |
| WO | WO 03/092779 A1 | 11/2003 | |

\* cited by examiner

*Primary Examiner* — Leslie Deak
*Assistant Examiner* — Sara Sass
(74) *Attorney, Agent, or Firm* — Birch, Stewart, Kolasch & Birch, LLP (57) ABSTRACT

A catheter assembly includes a catheter having on at least part of its surface a hydrophilic surface layer; a wetting fluid pouch including first and second layers of flexible material joined by a seal to form a sealed closure accommodating the wetting fluid; a receptacle forming a cavity for accommodation of the catheter and the wetting fluid pouch. The wetting fluid pouch is openable by compression of the wetting fluid pouch, thereby enabling the wetting fluid to be discharged into the receptacle. At least one of the first and second layers of the wetting fluid pouch extends beyond the seal of the sealed closure to form an attachment area outside the sealed closure, the wetting fluid pouch is attached to an inner surface of the receptacle, and the attachment being provided solely between the receptacle and the attachment area.

22 Claims, 6 Drawing Sheets

CATHETER ASSEMBLY COMPRISING A RECEPTACLE ACCOMMODATING A CATHETER AND A WETTING FLUID POUCH

CROSS REFERENCE TO RELATED APPLICATIONS

This nonprovisional application claims the benefit of U.S. Provisional Application No. 61/348,104 filed on May 25, 2010 and to Patent Application No. 10163767.6 filed in European Patent Office, on May 25, 2010. The entire contents of all of the above applications are hereby incorporated by reference into the present application.

TECHNICAL FIELD OF THE INVENTION

The present invention relates to a catheter assembly comprising a hydrophilic catheter, a wetting fluid pouch containing a wetting fluid for wetting the catheter, and a receptacle for accommodation of the catheter and the wetting fluid pouch. The invention further relates to a method for producing such a catheter assembly.

BACKGROUND

Catheters find their use in many different medical applications, such as urinary catheters for bladder drainage. Catheters are normally pre-packed in a receptacle by the manufacturer, in order to maintain the catheter in a clean and preferably sterile condition.

For many types of catheters, such as urinary catheters, it is desirable to have a slippery outer surface to facilitate insertion. For this reason hydrophilic urinary catheters may have a hydrophilic outer surface coating which should be wetted by a fluid such as water or saline for a certain time period prior to insertion thereof into the urethra of a patient. In order to facilitate the use and to improve cleanliness of the catheter, the assemblies have in recent years developed to comprise a rupturable wetting fluid pouch as well.

Thus, a typical catheter assembly of today may comprise a receptacle with a cavity for accommodation of the catheter and the wetting fluid pouch. However, as the wetting fluid pouch is loose it may fall out of the receptacle as the receptacle is opened to expose the catheter. To alleviate this problem, WO 01/52763 discloses a wetting fluid pouch affixed to a tear-off end of the receptacle. Thus, after the catheter has been wetted, the tear-off end can be torn off and removed from the receptacle along with the wetting fluid pouch for disposal thereof. Whereas such an opening procedure may be inconvenient for any user, the task becomes particularly demanding for users being disabled, such as users with limited capability of moving their limbs.

A more convenient catheter assembly is known from WO03/092779 disclosing a catheter assembly comprising a catheter receptacle including a compartment accommodating a wetting fluid. The compartment here forms an integrated part of the receptacle, but is separated by a separation wall including a point of weakness located between the wetting fluid compartment and the cavity containing the catheter. Hereby, the wetting fluid may be discharged into the cavity containing the catheter by compressing the wetting fluid compartment. However, whereas this solution alleviates the above discussed problems, the process of manufacturing a receptacle with an integrated wetting fluid compartment tends to be rather complex.

Thus, there is generally a problem to provide a catheter assembly that is easy to use, while also being easy and cost efficient to produce Consequently, there is a need for an alternative catheter assembly that alleviates the above-discussed problems.

SUMMARY OF THE INVENTION

It is therefore an object of the present invention to provide an alternative catheter assembly, which overcomes or at least alleviates the above-discussed problems of the prior art.

This object is achieved by means of the invention as defined in the appended claims.

According to a first aspect of the invention there is provided a catheter assembly comprising:

a catheter having on at least part of its surface a hydrophilic surface layer intended to produce a low-friction surface character of the catheter by treatment with a wetting fluid prior to use of the catheter;

a wetting fluid pouch comprising first and second layers of flexible material joined by a seal to form a sealed closure accommodating the wetting fluid;

a receptacle forming a cavity for accommodation of the catheter and the wetting fluid pouch, the wetting fluid pouch being openable by compression of the wetting fluid pouch, thereby enabling the wetting fluid to be discharged into the receptacle, wherein at least one of the first and second layers of the wetting fluid pouch extends beyond the seal of the sealed closure to form an attachment area outside the sealed closure, wherein the wetting fluid pouch is attached to an inner surface of the receptacle, the attachment being provided solely between the receptacle and the attachment area.

The flexible material used for wetting fluid pouch is preferably a flexible material which provides a moisture barrier or low water vapour transmission. The flexible material may e.g. comprise or consist of one or several of aluminum, aluminium oxide, silicone oxide, metallocene polyvinylidene chloride (PVdC) and poly(ethylene-vinylacetate) (EVA). For example, the flexible material can be made as coextruded polyolefines with polyamides, polyethylene terephtalate (PET), including barrier resins such as polyvinylidene chloride (PVdC) or poly(ethylene-vinylacetate) (EVA). However, other materials exhibiting similar properties are also feasible.

The present invention is based on the understanding that provision of an attachment area located outside of the seal of the wetting fluid pouch enables a firm attachment between the wetting fluid pouch and the receptacle. This prevents the wetting fluid pouch from falling out as the receptacle is opened and the catheter is pulled out from the receptacle, even if the wetting fluid pouch is located near the opening of the receptacle. As the wetting fluid pouch remains attached to the receptacle and can be disposed together with the receptacle, the opening procedure is facilitated, making the catheter assembly feasible also for disabled users, such as users with limited capability of moving their limbs. Furthermore, since the wetting fluid pouch remains attached to the receptacle, the risk of spilling any wetting fluid that remains in the wetting fluid pouch is reduced. Moreover, the wetting fluid pouch does not obstruct removal of the catheter.

The attachment area of the wetting fluid pouch may be attached to the inner surface of the receptacle by means of an adhesive, such as a medical grade adhesive, or by means of welding. The weld may be a spot weld or an elongated weld. The weld may be peelable or non-peelable. Since the attachment is made solely between the inner surface of the receptacle and the attachment area of the wetting fluid pouch, the risk of puncturing or otherwise damaging the wetting fluid pouch when welding is virtually eliminated. It also enables a cost efficient production of the catheter assembly.

Moreover, by keeping the wetting fluid pouch in a fixed position, it may be positioned to affect the receptacle as little as possible. This is advantageous as holes in the receptacle could contaminate the product which could be hazardous for the catheter user if it is not detected before use. The wetting fluid may also be positioned so that optimal density distribution is achieved when a plurality of catheter assemblies are arranged inside a secondary package and sterilized by e.g. e-beam. For sterilization with e-beam, even density distribution is to strive for in order to get a low dose ration and ensuring the sterility of all catheter assemblies.

Preferably, only one of the first and second layers of the wetting fluid pouch extends beyond the seal of the sealed closure to form a single layered attachment area. Advantages with a single layered attachment area are reduced consumption of material and a more pliable contact surface that can easily be attached to the receptacle.

According to an embodiment, the wetting fluid pouch may be formed by a single sheet of flexible material which is folded into the first and second layers of flexible material. Preferably, the sheet is folded such that an edge of the first layer of flexible material located opposite the fold and an edge of the second layer of flexible material located opposite the fold may be displaced relative each other, wherein the area between the edges forms the attachment area. This may be achieved by displacing the fold from a centre of the sheet of flexible material. This provides a convenient way of manufacturing a wetting fluid pouch provided with an attachment area having a single layer of flexible material.

According to another embodiment, the first and second layers of flexible material may be two initially separate sheets of flexible material joined by the seal to form the sealed closure. Preferably, the wetting fluid pouch may have a side where an edge of the first layer of flexible material and the edge of the second layer of flexible material are displaced relative each other, wherein the area between the edges forms the attachment area.

The receptacle may be provided with opening means enabling opening of the receptacle for removal of the catheter from said receptacle.

The opening means may comprise a peel-off joint. An advantage with a peel-off joint is that it is relatively easy to open also for disabled users, such as users with limited capability of moving their limbs. However, other openings means may also be utilized, such as a tear-off end.

The wetting fluid pouch may be arranged adjacent the opening means. This may be convenient as the receptacle may remain in the same position throughout the opening procedure. For example, the receptacle may be held such that the wetting fluid passes by gravity from the opened wetting fluid pouch to the portion of the receptacle where the insertion end of the catheter is located. The receptacle may then remain in that position as the receptacle is opened to take out the catheter.

Further, the wetting fluid pouch may be arranged between the catheter and the opening means. As the wetting fluid pouch and the catheter in this case are arranged tandemly (rather than overlying each other), the wetting fluid pouch may be compressed without pressing the catheter against the inner surface of the receptacle. This reduces the risk of holes or other damage to the receptacle. Furthermore, as the wetting fluid pouch is arranged next to the catheter, a lower dose ration can be used for sterilization of the catheter assembly when irradiation, such as e-beam, is used.

According to alternative embodiment, the wetting fluid pouch may overlie the catheter to achieve a more compact catheter assembly. In this case, it is preferred that the attachment area of the wetting fluid pouch is arranged to overly the catheter. Further, it is preferred that the sealed closure accommodating the wetting fluid does not overly the catheter, but instead be arranged transversely to the catheter. Hereby, the catheter assembly is still very compact in length and width, and also becomes relatively thin, since it only the thinnest part of the wetting fluid pouch overlies the catheter.

The attachment area which is attached to the receptacle may preferably be arranged on only one side of the wetting fluid pouch. This has the effect that the attachment between the wetting fluid pouch and the receptacle forms a hinged connection. As a result, the wetting fluid pouch does not obstruct the removal of the catheter from the receptacle as the wetting fluid pouch may move about the attachment to give way for the catheter.

The side of the wetting fluid pouch, where the attachment area is attached to the receptacle, may preferably be essentially parallel to an axial direction of the catheter. This further facilitates removal of the catheter from the receptacle as the catheter may slide along the attachment of wetting fluid pouch.

The attachment area may be provided at a side of the wetting fluid pouch essentially parallel to an axial direction of the catheter. This may facilitate removal of the catheter from the receptacle.

Furthermore, the attachment area may preferably be attached close to a side edge of the receptacle. This further reduces obstruction during removal of the catheter.

According to a second aspect of the invention there is provided a method for producing a catheter assembly, comprising the steps of:

providing a receptacle;
providing a hydrophilic catheter;
arranging the catheter in a cavity of the receptacle;
providing a wetting fluid pouch comprising first and second layers of flexible material joined by a seal to form a sealed closure for accommodation of said wetting fluid, wherein at least one of said first and second layers extends beyond the seal of the sealed closure to form an attachment area outside the sealed closure for attaching said wetting fluid pouch to said receptacle;
arranging the wetting fluid pouch containing the wetting fluid in the cavity of the receptacle; and
attaching the attachment area of said wetting fluid pouch to an inner surface of the receptacle.

This aspect of the invention provides similar advantages as discussed above in relation to the first aspect.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1A:
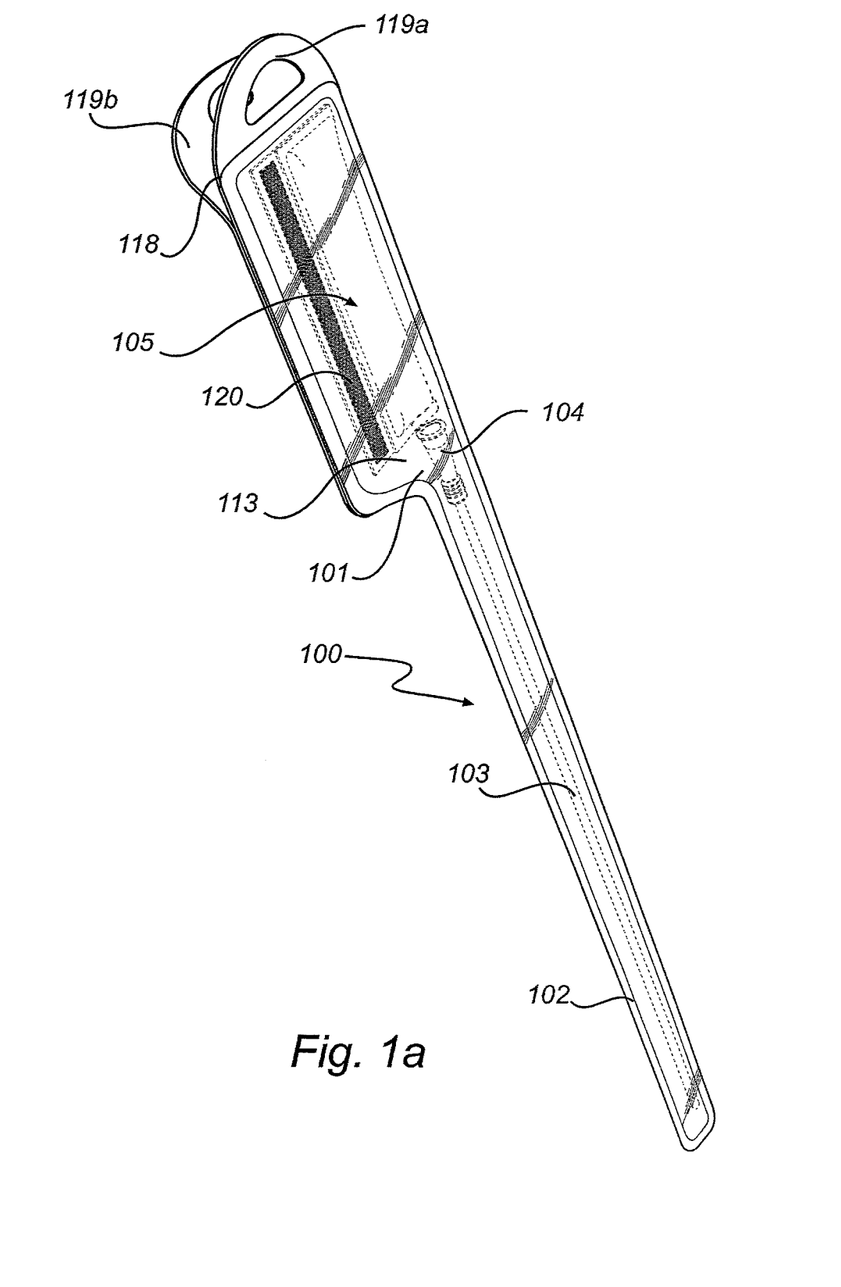
FIG. 1a-b schematically illustrates an embodiment of a catheter assembly where the wetting fluid pouch and the catheter are tandemly arranged.
Figure 1B:
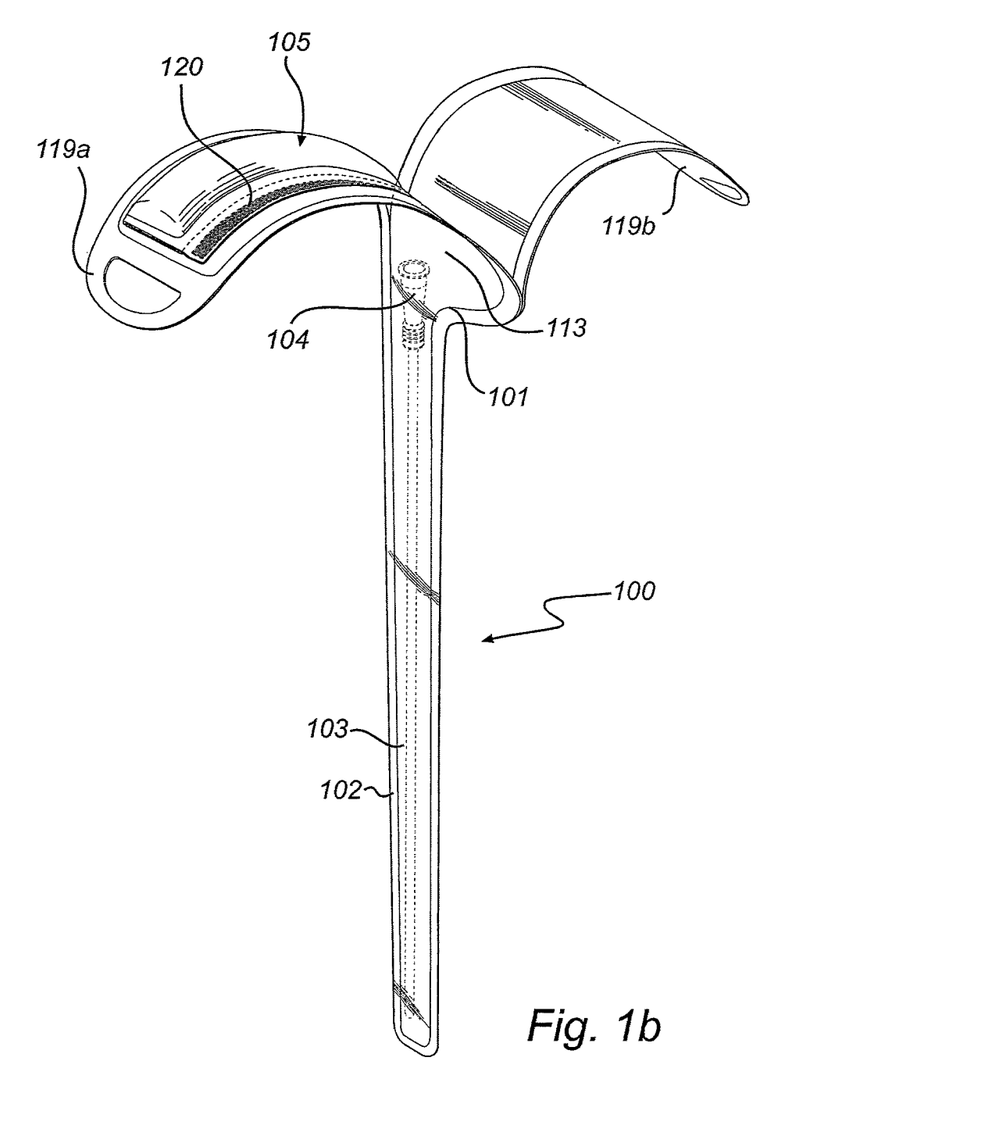
Figure 2A:
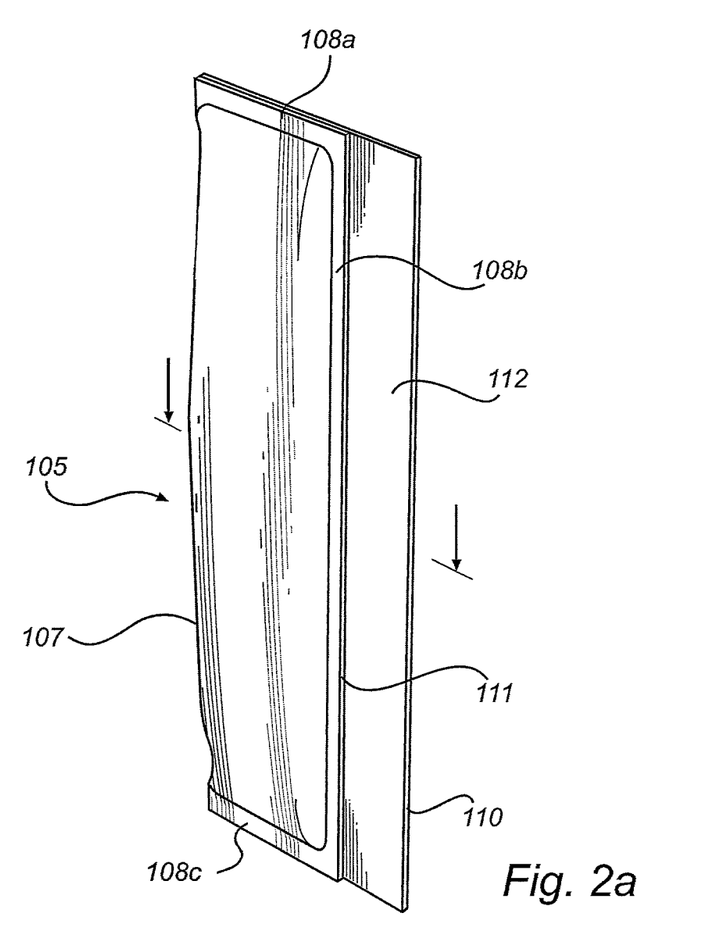
FIG. 2a-b schematically illustrates an embodiment of a wetting fluid pouch.
Figure 2B:
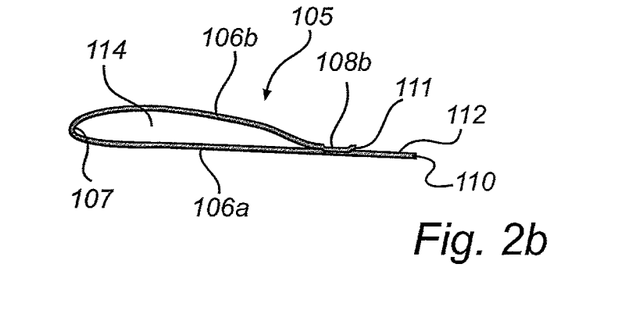

FIG. 1 schematically illustrates a catheter assembly 100 according to an embodiment of the invention. The catheter assembly 100 comprises a wetting receptacle 101 or bag. The receptacle is preferably of a flexible plastics material. The material may be transparent, but opaque or semi-opaque materials may also be used. For example, the receptacle can be made of polymer materials such as polyethen, polypropylene, polyamide, and PET, or the receptacle can be made from a laminate of such polymer materials and/or aluminum, aluminum oxide, or oriented polypropylene (OPP). The receptacle has a downwardly extending elongate pocket 102 at the forward end. The catheter assembly further comprises a hydrophilic urinary catheter 103, with a connector 104 for connection to other devices, such as a urine collection bag a drainage tube or the like. The catheter receptacle 101 is adapted for accommodation of the catheter, and at least the catheter tube is accommodated in the elongate pocket 102. Preferably, the receptacle 101 encloses the whole length of the catheter. Preferably, the receptacle comprises a narrow forward part 102 and a wider rearward part 113. The narrow forward part 102 is adapted to accommodate at least a part of the catheter, including the insertion end. It is possible to arrange essentially the entire catheter in the narrow part 102. Alternatively, at least a part of the catheter, including the outflow end (often referred to as connector end) extends into the wider rearward part 113. The catheter assembly also comprises a wetting fluid pouch 105 containing a wetting fluid (not illustrated). A more detailed view of the wetting fluid pouch is found in FIG. 2a-b. Referring to FIG. 2a-b, the wetting fluid pouch is here formed by a rectangular sheet of flexible material, such as an aluminum laminate, which sheet is folded along a folding line 107 into first 106a and second 106b layers of flexible material. The first and second layers of flexible material are joined by a seal so that the first 106a and second 106b layers form a sealed closure 114 for accommodation of the wetting fluid. Here the seal comprises three welds 108a-c. In this embodiment, the folding line 107 is parallel to, but displaced from a centre line of the rectangular sheet, such that an edge 110 of the first layer 106a of flexible material located opposite the fold 107 and an edge 111 of the second layer 106b of flexible material located opposite the fold 107, are parallel but displaced relative each other, wherein the portion of the first layer 106a of flexible material that extends beyond the edge 111 of the second layer 106b of material forms a single layered attachment area 112, or put differently, the area between the two edges 110, 111 forms the attachment area 112. It is recognized that either side of the single layered attachment area may be used to attach the wetting fluid pouch to the receptacle Referring to FIG. 1, the wetting fluid pouch 105 is here arranged in a part 113 of the receptacle extending rearwardly from the catheter 103, i.e. behind the connector 104 of the catheter. It should be noted that the rearward part 113 of the receptacle is in fluid communication with the forward part 102 housing the catheter 103.

Further, the wetting fluid pouch 105 is attached to the receptacle by at least one weld 120 provided between the attachment area 112 of the wetting fluid pouch and an inner surface of the receptacle. The weld 120 may extend over an elongated area as illustrated in FIG. 1, or be a spot weld. It is also possible to attach the attachment area to the receptacle with more than one weld. Alternative ways of attaching the attachment area 112 of the pouch to the inner surface of the receptacle may also be utilized, e.g. an adhesive, such as medical grade adhesive, can be used. In this embodiment, the side of the wetting fluid pouch where the attachment area 112 is arranged is essentially parallel to the extension of the catheter 103. This side of the wetting fluid pouch is here also the longer side of the pouch. It should be noted, however, that the attachment of the wetting fluid pouch to the receptacle preferably is provided solely between the attachment area and the receptacle.

The wetting fluid pouch 105 is preferably adapted such that moderate external pressure applied to the wetting fluid pouch will cause the sealed closure to rupture. This can be achieved by allowing the welds to separate as a result of the internal pressure induced when the wetting fluid pouch is compressed. For example, one of the three welds 108-c (or a portion thereof) can be made thinner than the other welds or have a point of weakness. Preferably, the weld of the side of the wetting fluid pouch which is to be arranged closest to the rearward end of the receptacle, i.e. the side to be farthest away from the insertion end of the catheter, is made weaker than the welds of the other sides. This will ensure that the wetting fluid will flow along essentially the whole receptacle when released.

Opening means 118 for opening the receptacle is here arranged rearwardly from the catheter 103, i.e. behind the connector 104 of the catheter, but on the other side of the wetting fluid pouch 105. The opening means may comprise e.g. a peelable joint 118 connected to tabs 119a-b extending from the edge for enabling opening of the receptacle by peeling the tabs 119a-b apart, thereby separating the foil walls of the receptacle.

In order to prepare the catheter for catheterization, a compression force is applied to the wetting fluid pouch 105 in such a way that the sealed closure 114 is ruptured and wetting fluid is discharged into the receptacle. This may be achieved without opening the receptacle, whereby the sterile environment of the receptacle is still maintained during this step. The receptacle may preferably be held vertically with the wetting fluid pouch above the catheter, so that the wetting fluid is passed by gravity into the elongate pocket 102 that accommodates the catheter 103. Preferably, the wetting fluid pouch contains a sufficient amount of wetting fluid for the insertable length of the catheter to be sufficiently wetted. After release of the wetting fluid into the elongate pocket 102 the receptacle can be opened by grabbing and peeling the tabs 119a-b to separate the foil walls at the end of the receptacle. The receptacle is preferably arranged to allow a sufficient degree of separation of the foil walls so that the catheter 103 can be easily grabbed at the connector 104 and be pulled out of the receptacle.

Thus, the portion of the receptacle where the wetting fluid pouch is arranged can be folded away by separating the foil walls all the way down to the connector of the catheter. It should be noted that although this portion of the receptacle is more or less turned inside out, the wetting fluid pouch will remain affixed to the receptacle by the attachment weld 120. Thus, as the catheter has been removed the receptacle 101 may be disposed along with the wetting fluid pouch 105.

Figures 3A, 3B:
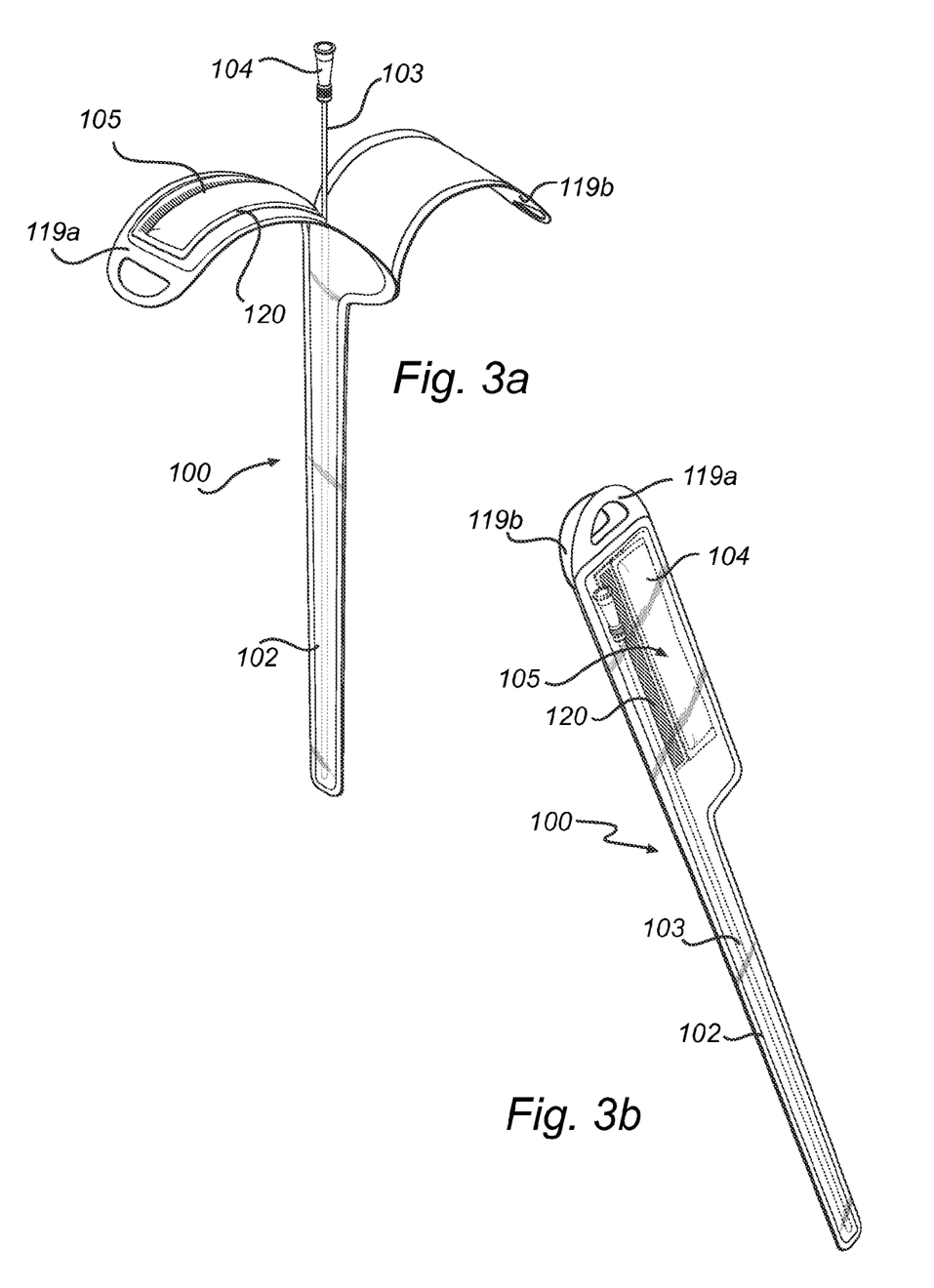
FIG. 3a-b schematically illustrates an embodiment of a catheter assembly where the wetting fluid pouch overlie the catheter.

FIG. 3 illustrates an alternative embodiment of a catheter assembly. This embodiment resembles the embodiment discussed with reference to FIG. 1 and FIG. 2, but instead of having the catheter 103 and the wetting fluid pouch 105 tandemly arranged, the wetting fluid pouch overlies the catheter, enabling a more compact catheter assembly. In this embodiment, it may suffice to separate the foil walls at the very end of the receptacle to provide an opening that allows the catheter 103 to be grabbed at the connector 104. The catheter may then be pulled out next to the wetting fluid pouch. Since the wetting fluid pouch is attached along one side only, and since the attachment side of the pouch is parallel to the axial direction of the catheter, the pouch may move about the attachment to give way for the catheter as it is pulled out of the catheter. As the wetting fluid pouch remains inside the receptacle throughout the opening procedure, the risk of spilling any wetting fluid that remains inside the wetting fluid pouch is reduced.

A production method of the wetting fluid pouch will now be described with reference to FIG. 2. In a production method of the wetting fluid pouch 105, the pouch may be formed by providing a rectangular sheet of flexible material, such as an aluminum laminate; folding the sheet along a folding line 107 parallel to, but displaced from, the centre line of the sheet to a first 106a and second 106b layers of flexible material; and providing a longitudinal weld 108b to join the two layers, wherein the weld is arranged along the edge 111 of the less wide layer 106b. This results in a tube of flexible material. The tube is filled with wetting fluid (e.g. water or saline) and transversally welded to form sealed closures 114 containing the wetting fluid. Cuts are made in the transversal welding areas so that each sealed closure is separated from the others to form a wetting fluid pouch. The single layer of material that remains outside the longitudinal weld 108b forms an attachment area for attaching the wetting fluid pouch to the receptacle.

In a production method of the catheter assembly 100, the receptacle 101 is manufactured, and the catheter 103 and the wetting fluid pouch 105 are arranged inside the receptacle 101. An attachment area 112 of the wetting fluid pouch is attached to an inner surface of the receptacle. Then, the assembly 100 may be sterilized. Sterilization of the catheter may be achieved by irradiation by an e-beam in which case the fluid in the wetting fluid pouch could be sterilized when assembled, at the same time as the rest of the components of the assembly. Since the wetting fluid pouch is kept in a fixed position, it may preferably be positioned for optimal density distribution. When sterilized with e-beam, even density distribution is to strive for in order to get a low dose ration and ensuring the sterility of the catheter assembly.

Furthermore, the wetting fluid pouch may preferably be positioned so that it will have as little affect as possible on the receptacle. For example, it is preferred to arrange the wetting fluid pouch so that the outer sides of the wetting fluid pouch do not lie in direct contact with the inner sides of the receptacle, but arranged at a certain distance from said inner sides. This is advantageous as holes in the receptacle could contaminate the product which could be hazardous for the catheter user if it is not detected before use. To the same end, the wetting fluid pouch is preferably made free from sharp corners, especially at parts distant from the attachment area, e.g. by provision of rounded corners.

Figure 4:
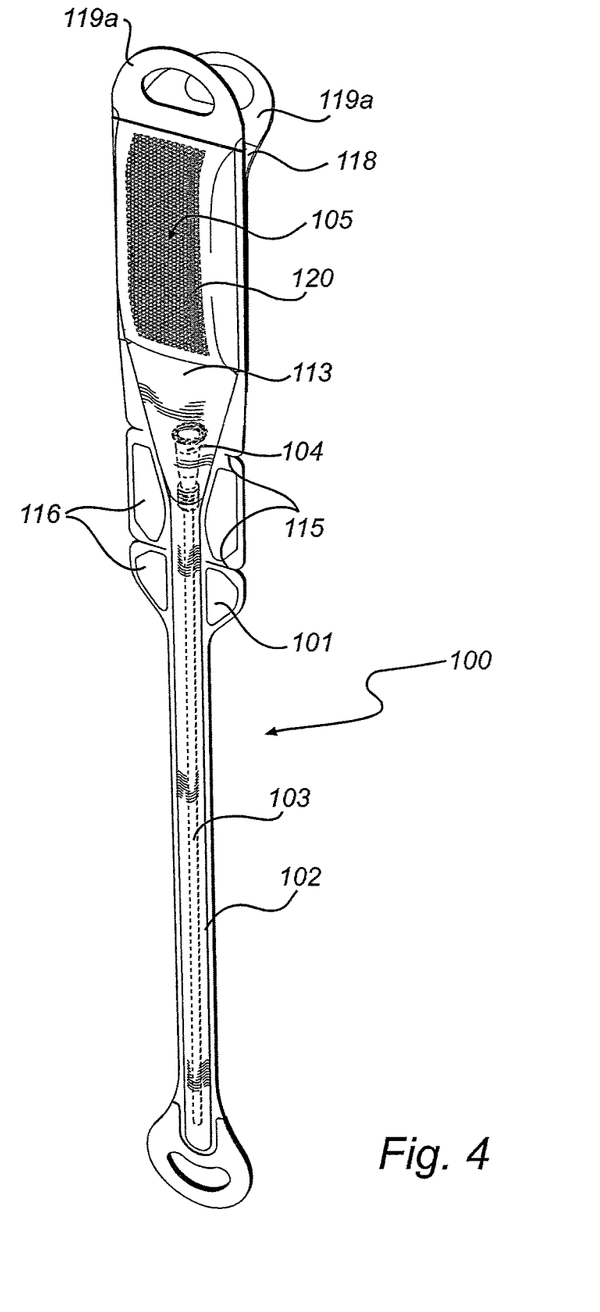
FIG. 4 schematically illustrates an alternative embodiment of a catheter assembly.

FIG. 4 illustrates another embodiment of the catheter assembly. This embodiment resembles the embodiment discussed with reference to FIGS. 1 and 2, but is provided with additional opening means offering alternative ways to remove the catheter from the receptacle. The additional opening means are here in the form of tear lines 115 arranged at the elongate pocket 102 of the receptacle. The tear lines are connected to one or several gripping handles 116, such as a pulling tab.

Figure 5A:
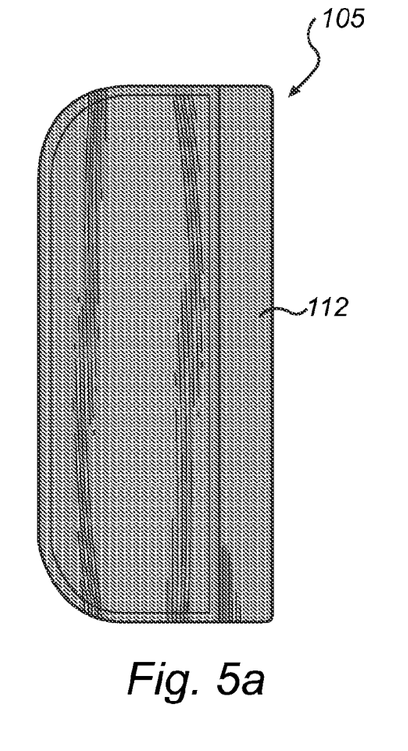
FIGS. 5a-5c schematically illustrates alternative embodiments of a wetting fluid pouch.

FIG. 5a illustrates another embodiment of a wetting fluid pouch. This embodiment resembles the embodiment discussed above with reference to FIG. 2, but two corners of the wetting fluid pouch are rounded, which corners are located on a side of the wetting fluid pouch opposite to the side with the attachment area 112. This may further facilitate the removal of the catheter from the receptacle. As discussed above, rounded corners also reduces the risk of damaging the receptacle. Still further, the pressure and stress obtained with rounded corners is less concentrated compared to sharp corners, thereby minimizing the risk of leakage at the corners.

Figure 5B:
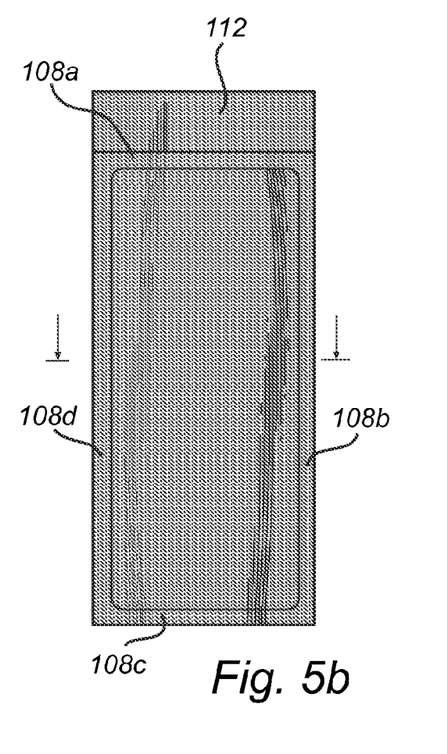
Figure 5C:
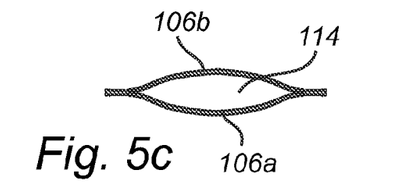

FIG. 5b illustrates yet another embodiment of a wetting fluid pouch. Here the first 106a and second 106b layers of flexible material are two initially separate rectangular sheets of flexible material joint by a seal to form the sealed closure 114. The two sheets have the same width, but the first sheet 106a is longer than the second sheet 106b. The sheets are arranged on top of each other edge to edge, except for one side (here the upper side) where the edge of the first sheet and the edge of the second sheet are displaced relative each other. The area 112 between the edges forms the attachment area. In this embodiment, the seal comprises four welds 108a-d provided along the edge of the smaller sheet. Similarly, a wetting fluid pouch with a first attachment area on a first side, and a second attachment area on a second side (opposite the first side), can be achieved by displacing two sheets having the same size relative each other.

Specific embodiments of the invention have now been described. However, several alternatives are possible, as would be apparent for someone skilled in the art. For example, although the wetting fluid pouch in the described embodiments has been arranged close to the connector of the catheter, the pouch may also be arranged close to the insertion end of the catheter, or in any other suitable location in the assembly. It is also possible to have a wetting fluid pouch with an attachment area along more than one side of the wetting fluid pouch, and attaching the wetting fluid pouch to the receptacle using one or more of these attachment areas.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A catheter assembly comprising:
   a catheter having on at least part of its surface a hydrophilic surface layer intended to produce a low-friction surface character of the catheter by treatment with a wetting fluid prior to use of the catheter;
   a wetting fluid pouch comprising first and second layers of flexible material joined by a seal to form a sealed closure accommodating said wetting fluid;
   a receptacle forming a cavity for accommodation of said catheter and said wetting fluid pouch,
   said wetting fluid pouch being openable by compression of said wetting fluid pouch, thereby enabling the wetting fluid to be discharged into the receptacle,
   wherein at least one of said first and second layers of said wetting fluid pouch extends beyond the seal of the sealed closure to form an attachment area outside the sealed closure, wherein said wetting fluid pouch is attached to an inner surface of said receptacle, said attachment being provided solely between the receptacle and said attachment area, and wherein the wetting fluid pouch is, in its entirety, accommodated within the cavity of the receptacle with the sole attachment, formed only between the inner surface of the receptacle and the attachment area, to the receptacle, and formation of the sealed closure of the wetting fluid pouch is independent of formation of the cavity of the receptacle.

2. The catheter assembly according to claim 1, wherein only one of said first and second layers of said wetting fluid pouch extends beyond the seal of the sealed closure to form a single layered attachment area.

3. The catheter assembly according to claim 1, wherein the wetting fluid pouch is formed by a single sheet of flexible material which is folded into said first and second layers of flexible material.

4. The catheter assembly according to claim 3, wherein an edge of the first layer of flexible material located opposite the fold and an edge of the second layer of flexible material located opposite the fold are displaced relative each other, wherein the area between the edges forms said attachment area.

5. The catheter assembly according to claim 1, wherein the first and second layers of flexible material are two initially separate sheets of flexible material joined by said seal to form the sealed closure.

6. The catheter assembly according to claim 5, wherein the wetting fluid pouch has a side where an edge of the first layer of flexible material and the edge of the second layer of flexible material are displaced relative each other, wherein the area between the edges forms the attachment area.

7. The catheter assembly according to claim 1, wherein the receptacle is provided with opening means enabling opening of said receptacle for removal of the catheter from said receptacle.

8. The catheter assembly according to claim 7, wherein the opening means comprises a peel-off joint.

9. The catheter assembly according to claim 7, wherein said wetting fluid pouch is arranged adjacent said opening means.

10. The catheter assembly according to claim 7, wherein said wetting fluid pouch is arranged between said catheter and said opening means.

11. The catheter assembly according to claim 1, wherein said wetting fluid pouch overlies the catheter with the at least one of said first and second layers of said wetting fluid pouch extending beyond the seal of the sealed closure to form the attachment area outside the sealed closure.

12. The catheter assembly according to claim 1, wherein the attachment area which is attached to the receptacle is arranged on only one side of the wetting fluid pouch.

13. The catheter assembly according to claim 12, wherein the side of the wetting fluid pouch where the attachment area is attached to the receptacle, is essentially parallel to an axial direction of the catheter.

14. The catheter assembly according to claim 1, wherein said attachment area is welded to the inner surface of the receptacle.

15. The catheter assembly according to claim 1, wherein said attachment area is attached to the inner surface of the receptacle by an adhesive.

16. The catheter assembly according to claim 1, wherein said attachment area is attached close to a side edge of the receptacle.

17. A method for producing a catheter assembly, comprising the steps of:
providing a receptacle;
providing a hydrophilic catheter;
arranging the catheter in a cavity of the receptacle;
providing a wetting fluid pouch comprising first and second layers of flexible material joined by a seal to form a sealed closure for accommodation of said wetting fluid, wherein at least one of said first and second layers extends beyond the seal of the sealed closure to form an attachment area outside the sealed closure for attaching said wetting fluid pouch to said receptacle;
arranging the wetting fluid pouch containing the wetting fluid in the cavity of the receptacle; and
attaching the attachment area of said wetting fluid pouch to an inner surface of the receptacle, and
wherein the wetting fluid pouch is, in its entirety, accommodated within the cavity of the receptacle with the sole attachment, formed only between the inner surface of the receptacle and the attachment area, to the receptacle, and formation of the sealed closure of the wetting fluid pouch is independent of formation of the cavity of the receptacle.

18. The catheter assembly according to claim 2, wherein the wetting fluid pouch is formed by a single sheet of flexible material which is folded into said first and second layers of flexible material.

19. The catheter assembly according to claim 2, wherein the first and second layers of flexible material are two initially separate sheets of flexible material joined by said seal to form the sealed closure.

20. The catheter assembly according to claim 2, wherein the receptacle is provided with opening means enabling opening of said receptacle for removal of the catheter from said receptacle.

21. The catheter assembly according to claim 1, wherein the seal forming the sealed closure of the wetting fluid pouch is different from a seal forming the sole attachment between the inner surface of the receptacle and the attachment area of the wetting fluid pouch.

22. The method according to claim 17, wherein the seal forming the sealed closure of the wetting fluid pouch is different from a seal forming the sole attachment between the inner surface of the receptacle and the attachment area of the wetting fluid pouch.

* * * * *